United States Patent
Kahaian et al.

(10) Patent No.: US 10,078,073 B2
(45) Date of Patent: Sep. 18, 2018

(54) MULTI-COMPARTMENT PACKAGE

(71) Applicant: Ecolab USA Inc., St. Paul, MN (US)

(72) Inventors: Arthur J. Kahaian, Chicago, IL (US); Sasha J. Welz, Chicago, IL (US); Joe L. Schwartz, Aurora, IL (US); Adam J. Bauer, Johnstown, CO (US); Lyle Sampson, Loveland, CO (US)

(73) Assignee: Ecolab USA Inc., St. Paul, MN (US)

( * ) Notice: Subject to any disclaimer, the term of this patent is extended or adjusted under 35 U.S.C. 154(b) by 283 days.

(21) Appl. No.: 14/483,634

(22) Filed: Sep. 11, 2014

(65) Prior Publication Data

US 2015/0079688 A1    Mar. 19, 2015

Related U.S. Application Data

(60) Provisional application No. 61/877,811, filed on Sep. 13, 2013.

(51) Int. Cl.
*G01N 33/18* (2006.01)
*B01L 3/00* (2006.01)

(52) U.S. Cl.
CPC .......... *G01N 33/1813* (2013.01); *B01L 3/505* (2013.01); *B01L 3/523* (2013.01); *B01L 2200/16* (2013.01); *B01L 2300/042* (2013.01); *B01L 2400/0481* (2013.01); *B01L 2400/0683* (2013.01)

(58) Field of Classification Search
CPC ............................ G01N 33/1813; B01L 3/523
See application file for complete search history.

(56) References Cited

U.S. PATENT DOCUMENTS 3,741,727 A * 6/1973 Stroterhoff ............... G01N 1/10
                                            422/510
3,986,834 A * 10/1976 Steinbrink, Jr. ....... G01N 33/62
                                            206/219
4,205,955 A * 6/1980 Sloat .................. G01N 33/1853
                                            436/175

(Continued)

FOREIGN PATENT DOCUMENTS

| EP | 0536059 A2 | 4/1993 |
| WO | WO 2007/130904 | 11/2007 |
| WO | WO 2009/149024 | 12/2009 |

OTHER PUBLICATIONS

Fluorimetric sequential injection determination of magnesium using 8-hydroxiquinolie-5-sulfonic acid in a micellar medium G. de Armas, A. Cladera, E. Becerra, J.M. Estela, V. Cerda Talanta 52 (2000) 77-82.*

(Continued)

*Primary Examiner* — Krishnan S Menon
*Assistant Examiner* — Dwan A Gerido
(74) *Attorney, Agent, or Firm* — Leydig, Voit & Mayer, Ltd.

(57) ABSTRACT

A package comprising a body comprising a first compartment containing a first substance and a second compartment containing a second substance. The package includes a first state in which the first compartment is isolated from the second compartment such that the first substance is separated from the second substance, and a second state in which the first compartment communicates with the second compartment such that the first substance and the second substance combine.

20 Claims, 4 Drawing Sheets

(56) References Cited

U.S. PATENT DOCUMENTS

| | | | | |
|---|---|---|---|---|
| 4,647,541 | A * | 3/1987 | Guadagno | C12Q 1/28 |
| | | | | 422/413 |
| 5,550,061 | A * | 8/1996 | Stone | G01N 33/84 |
| | | | | 422/412 |
| 5,554,268 | A * | 9/1996 | Priddy | G01N 33/1813 |
| | | | | 204/400 |
| 5,912,180 | A * | 6/1999 | Stone | G01N 1/34 |
| | | | | 436/164 |
| 6,790,666 | B2 * | 9/2004 | Dang | G01N 21/643 |
| | | | | 436/172 |
| 2004/0247628 | A1 | 12/2004 | Lintz et al. | |
| 2005/0087456 | A1 | 4/2005 | Oka et al. | |
| 2007/0080078 | A1 * | 4/2007 | Hansen | B65D 81/3266 |
| | | | | 206/219 |
| 2007/0144923 | A1 | 6/2007 | Houwaert et al. | |
| 2007/0261974 | A1 | 11/2007 | Balteau et al. | |
| 2010/0069817 | A1 * | 3/2010 | Falkvall | A61M 1/1656 |
| | | | | 604/6.11 |
| 2010/0249699 | A1 | 9/2010 | Roy et al. | |

OTHER PUBLICATIONS

KIPO, International Search Report in International Patent Application No. PCT/US2014/055168, dated Dec. 23, 2014, 4 pp.
KIPO, Written Opinion in International Patent Application No. PCT/US2014/055168, dated Dec. 23, 2014, 6 pp.
European Patent Office, Extended European Search Report in European Patent Application No. 14843383.2, dated Apr. 21, 2017, 8 pp.

\* cited by examiner

//  MULTI-COMPARTMENT PACKAGE

This application claims the benefit of U.S. Provisional Patent Application Ser. No. 61/877,811, filed Sep. 13, 2013, the disclosure of which is incorporated herein by reference in its entirety.

TECHNICAL FIELD

The present invention relates to packages for storing substances and methods of manufacturing and using the same.

BACKGROUND

Component separation, where one component is mixed with another component, has been applied in the food and medical fields. Generally, substances used in water analysis, for example, in the paper industry, waste water treatment industry or energy industry, utilize either premixed or point-of-use packaging. An exemplary embodiment of "point-of-use packaging" utilizes a solid reagent in a package that is mixed with a solvent (e.g., water) on site. A disadvantage of point-of-use packaging occurs when the solid reagent is mis-dosed or does not become completely dissolved, thereby not providing accurate results.

Typical water analysis packages include a solute and a solvent or fluid mixed together in a pre-mixed solution. Generally, the solute has a finite degradation once dissolved, and therefore the pre-mixed solution has a limited shelf-life and lifetime for use. Degradation may be caused by one or more of several factors, including, inter alia, heat, light, presence of oxidants and/or other stresses. When in pre-mixed solution, degradation is often more severe such that the lifetime of the solute, and therefore the solution, is even further limited.

Accordingly, there is a need for point-of-use reagents and solvents for water analysis applications that enable the reagent and solvent to be easily shipped and have an extended lifetime. In addition, there is a need for easy-to-use mixing and application of these solutions to enable proper and efficient water analysis in industry.

SUMMARY OF INVENTION

In one aspect, the invention provides a package including a body having a first wall and a second wall extending between a first end and a second end. The first and second walls are coupled to one another to define a periphery of the package. The package further includes a seal coupling the first wall to the second wall between the first end and the second end. The seal defines a first compartment and a second compartment, and is breakable to allow communication between the first compartment and the second compartments.

In another aspect, the invention provides a package including a body including a first compartment having a first substance and a second compartment having a second substance. The package includes a first state in which the first compartment is isolated from the second compartment such that the first substance is separated from the second substance, and a second state in which the first compartment communicates with the second compartment such that the first substance and the second substance mix.

In yet another aspect, the invention provides a package including a body having a first compartment comprising a liquid, a second compartment comprising a reagent for water analysis, and a breakable seal that separates the first and second compartments, wherein when the breakable seal is broken via the application of physical force, the reagent and liquid forming a mixture.

In yet another aspect, the invention provides a method of use of a package including providing a body having a first compartment having a first substance and a second compartment having a second substance. The first compartment is separated from the second compartment by a breakable seal. The method further comprises breaking the seal, and combining the first substance and the second substance.

In another aspect, the invention provides a method for analyzing one or more properties of water comprising: (a) providing a package that includes a body having a first compartment comprising a liquid, a second compartment comprising a reagent for water analysis, and a breakable seal that separates the first and second compartments; (b) breaking the breakable seal via physical force, thereby providing for the formation of a mixture comprising the reagent and liquid; (c) adding the mixture to the water; and (d) analyzing the one or more properties of the water.

In another aspect, the invention provides a method of manufacturing a package including providing a body including a first wall and a second wall extending between a first and a second end. The first and second walls are coupled to one another to define a periphery of the package. The method further includes coupling the first wall to the second wall between the first and the second end to define a first compartment for enclosing a first substance and a second compartment for enclosing a second substance.

Other aspects of the invention will become apparent by consideration of the detailed description and accompanying drawings.

DETAILED DESCRIPTION

Figure 1:
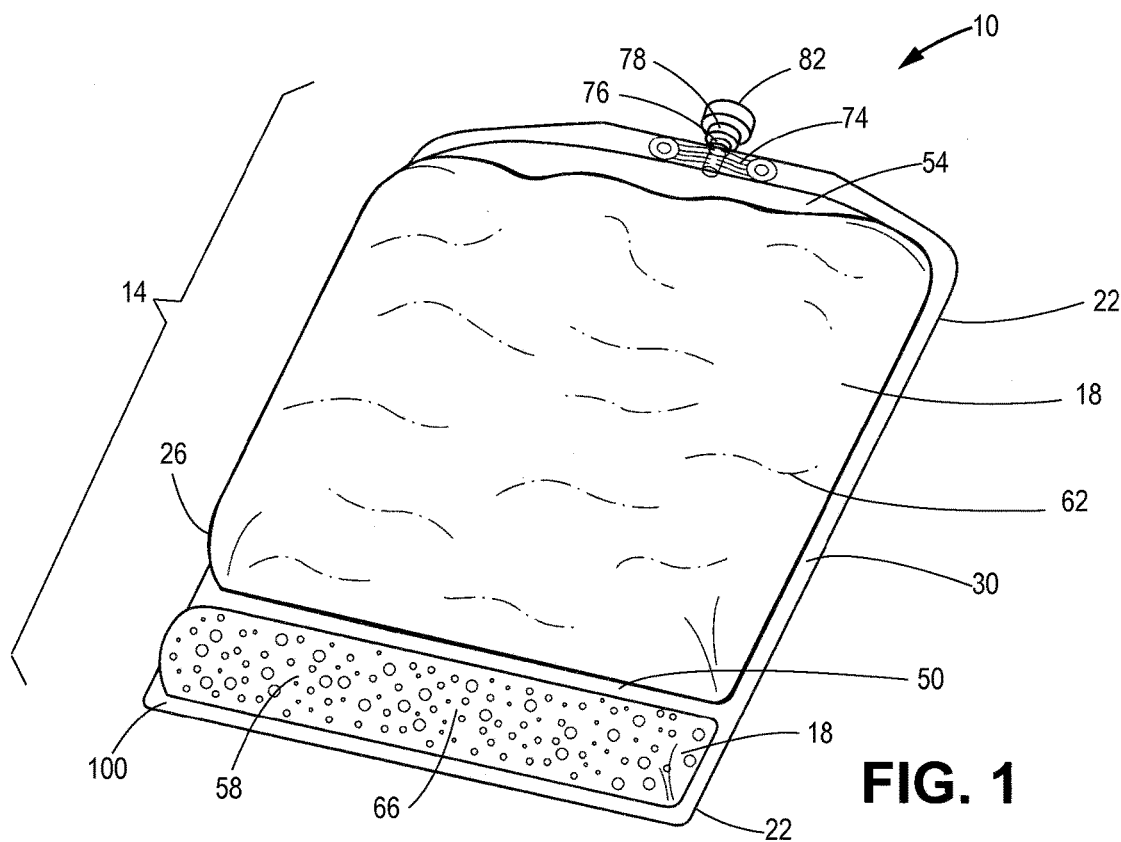
FIG. 1 is a perspective view of a package according to one embodiment and including a first state in which a first compartment is separate from a second compartment.

While embodiments encompassing the general inventive concepts may take various forms, there is shown in the drawings and will hereinafter be described various embodiments with the understanding that the present disclosure is to be considered merely an exemplification and is not intended to be limited to the specific embodiments.

The present invention is directed to a point of use packaging for water analysis applications that provide both the reagent and solvent an extended lifetime before use as a mixed solution. The package incorporates a breakable seal internal to the bag dimension. The breakable seal is said to be "temporary," i.e., not strong enough to open with common pressure from shipping and handling, or air freight shipment. However, when the reagent is ready to be added to the solution at the point of use, the seal will release with delivery of pressure allowing the separate components to mix. For example, the pressure may be applied via hand pressure. Accordingly, the package allows for a reagent having limited chemical stability when dissolved to have an extend shelf life. In a preferred embodiment, the substances contained in the package are pre-measured, multi-component formulations.

Before any embodiments of the invention are explained in detail, it is to be understood that the invention is not limited in its application to the details of construction and the arrangement of components set forth in the following description or illustrated in the following drawings. The invention is capable of other embodiments and of being practiced or carried out in various ways.

FIGS. 1-4 illustrate a package 10 including a body 14 having a first wall 18 and a second wall 22 extending between a first end 26 and a second end 30. The first wall 18 is coupled to the second wall 22 to create a peripheral seal 100 of the package 10. Each of the first wall 18 and the second wall 22 includes an exterior surface 34 and an interior surface 38. The interior surface 38 of the first wall 18 faces the interior surface 38 of the second wall 22. In certain embodiments of the package 10, the body 14 is constructed of any suitable material, and is preferably a thermoplastic polymer. Examples of thermoplastic polymers include, but are not limited to, polyethylene, polypropylene, polystyrene, polyethylene terephthalate, nylon, polycarbonate, polyvinyl chloride, polytetrafluoroethylene, polyurethane, polyamide, polyacrylamide, copolymers thereof, and blends thereof. In certain embodiments, the thermoplastic polymer is virgin, i.e., contains no recycled material. In certain embodiments of the package 10, the first wall 18 and the second wall 22 are constructed from a single material (e.g., polypropylene). The exterior surface 34 of the package 10 may include additional layers formed from a variety of materials including, for example, a polyester layer and/or a nylon layer. The walls 18, 22 of the package contacting the substances should be constructed of materials that are capable of containing the substances. The materials of construction should be selected so as to avoid facilitating degradation of themselves and of the substances contained therein.

Figure 2:
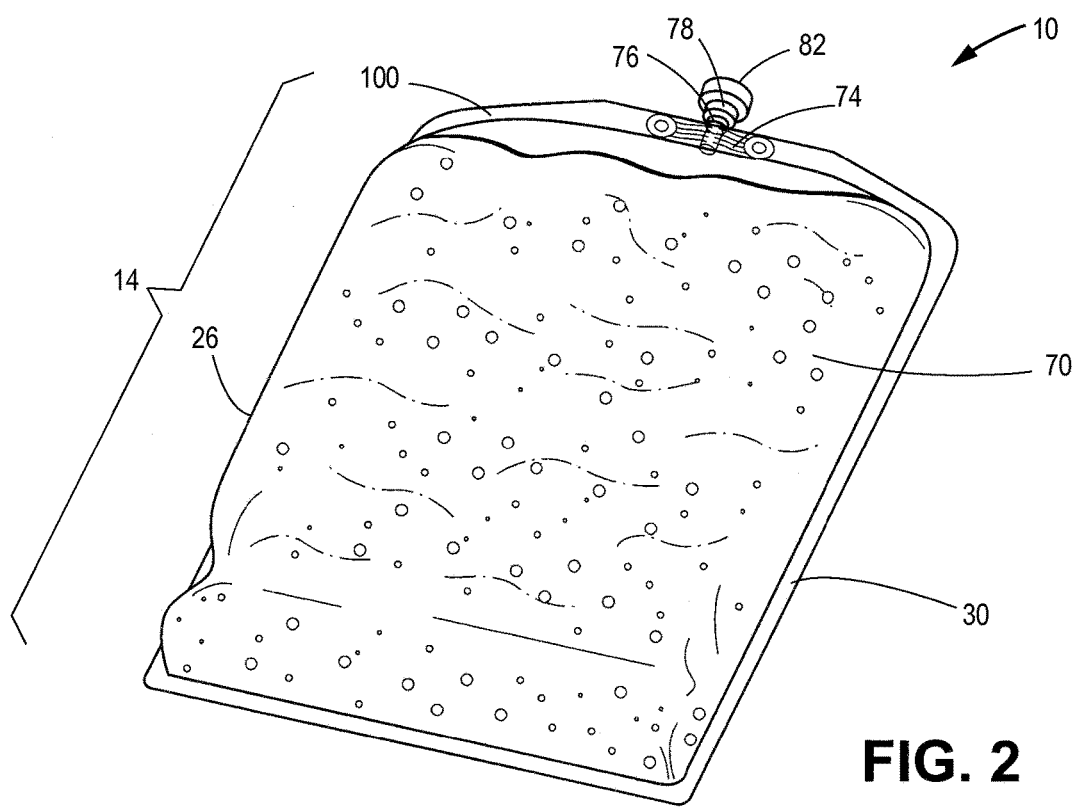
FIG. 2 is a perspective view of the package of FIG. 1 including a second state in which the first compartment is in communication with the second compartment.
Figure 3:
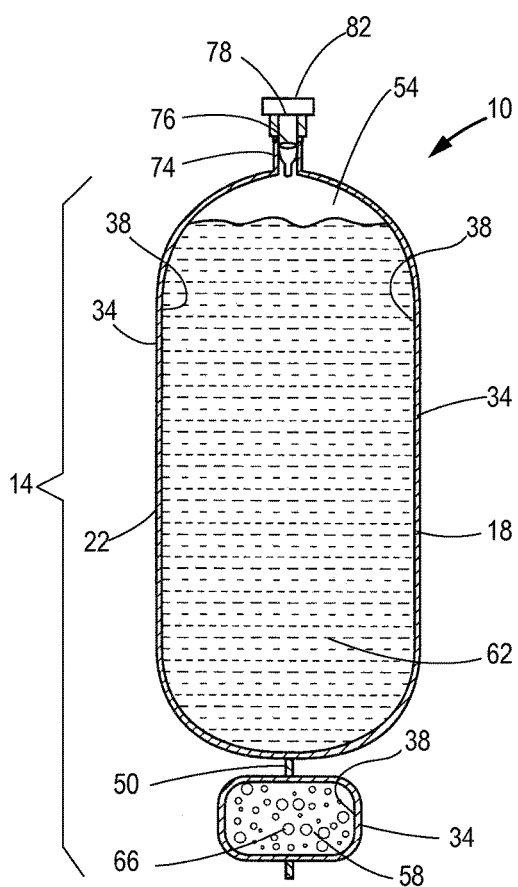
FIG. 3 is a cross-sectional view of the package of FIG. 1 while the package is in the first state.
Figure 4:
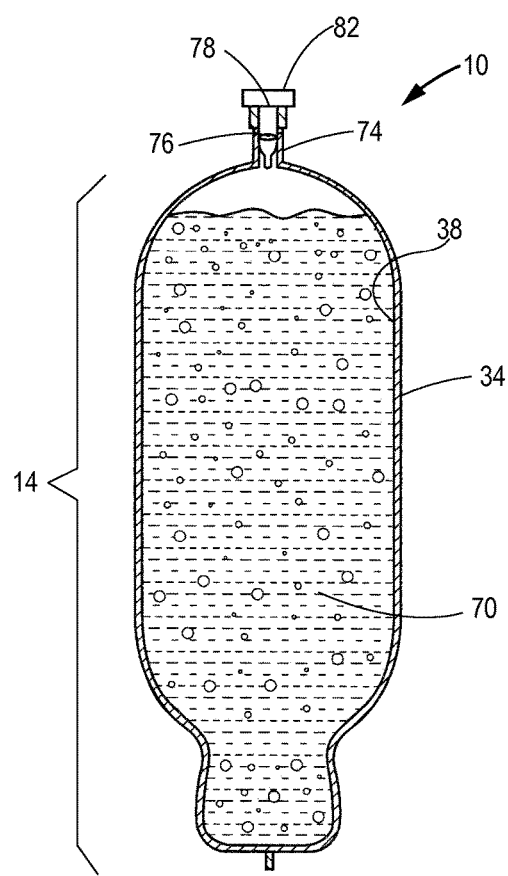
FIG. 4 is a cross-sectional view of the package of FIG. 2 while the package is in the second state.

Further with respect to FIG. 1 the package 10 includes at least one breakable seal 50 defining at least a first compartment 54 and a second compartment 28. In particular, a portion of the interior surface 38 of the first wall 18 is coupled to a portion of the interior surface 38 of the second wall 22. The breakable seal 50 may be created using, for example, heat sealing, induction sealing, and ultrasonic welding. The first compartment 54 contains a first substance 62 while the second compartment 58 contains a second substance 66. The breakable seal 50 separates the first substance 62 and the second substance 66 from one another (FIGS. 1 and 3). When desired, the end user breaks the breakable seal 50 by applying, e.g., hand pressure, thereby allowing the first substance 62 and the second substance 66 to combine into, e.g., solution 70 (FIGS. 2 and 4). In the illustrative embodiment, the first substance 62 is a liquid, e.g., a solvent. In certain embodiments of the illustrative embodiment, the first substance 62 comprises water. In the illustrative embodiment, the second substance 66 is a solute, which also may be a liquid and/or comprise water. In certain embodiments of the illustrative embodiment, the solute comprises a solid. While the illustrated embodiment comprises one breakable seal and two compartments, there may be additional breakable seals defining additional compartments (e.g., n compartments) in additional or alternative embodiments.

The body 14 further includes an outlet 74. The outlet 74 may be equipped with a nozzle 76 having valve 78 that defines an opening 82. The valve 78 allows the solution 70 to be selectively expelled through opening 82. In the illustrated embodiment, the valve 78 is fluidly connected to the first compartment, although in additional or alternative embodiments the outlet may be fluidly connected to the second or any compartment, including more than one compartment. In certain embodiments of the package 10, the valve 78 is a luer lock valve, which in certain embodiments is constructed of the same material as the body 14 (e.g., polypropylene). In embodiments where both the body 14 and the valve 78 are formed from polypropylene, contaminants are not introduced into the materials of the package 10. In certain embodiments of the package 10, the valve 78 is selected from the group consisting of: a gate valve, a globe valve, a ball valve, and butterfly valve.

In certain embodiments, the package 10 may include at least one reinforced area, which in certain embodiments is formed by, e.g., a wide heat seal region. For example, in the embodiment illustrated in FIG. 5, the package 10 includes a first reinforced area 86 and a second reinforced area 90. The first and second reinforced areas 86, 90 each include through-holes 94 such that the package 10 may be suspended prior to or during use. In the illustrated embodiment, the first and second reinforced areas 86, 90 are located on opposite sides of the first compartment 54, and each of the first and second reinforced areas 86, 90 include two through-holes 94 extending there through. The reinforced areas may be located at other locations along the periphery other than what is shown and described herein. Additionally, there may be more or fewer through-holes.

The first compartment 54, and therefore the package 10, is configured to hold anywhere from about 1 liter to about 20 liters of fluid. Preferably, the first compartment 54 is configured to hold from about 1 liter to about 2 liters of fluid.

Figure 5:
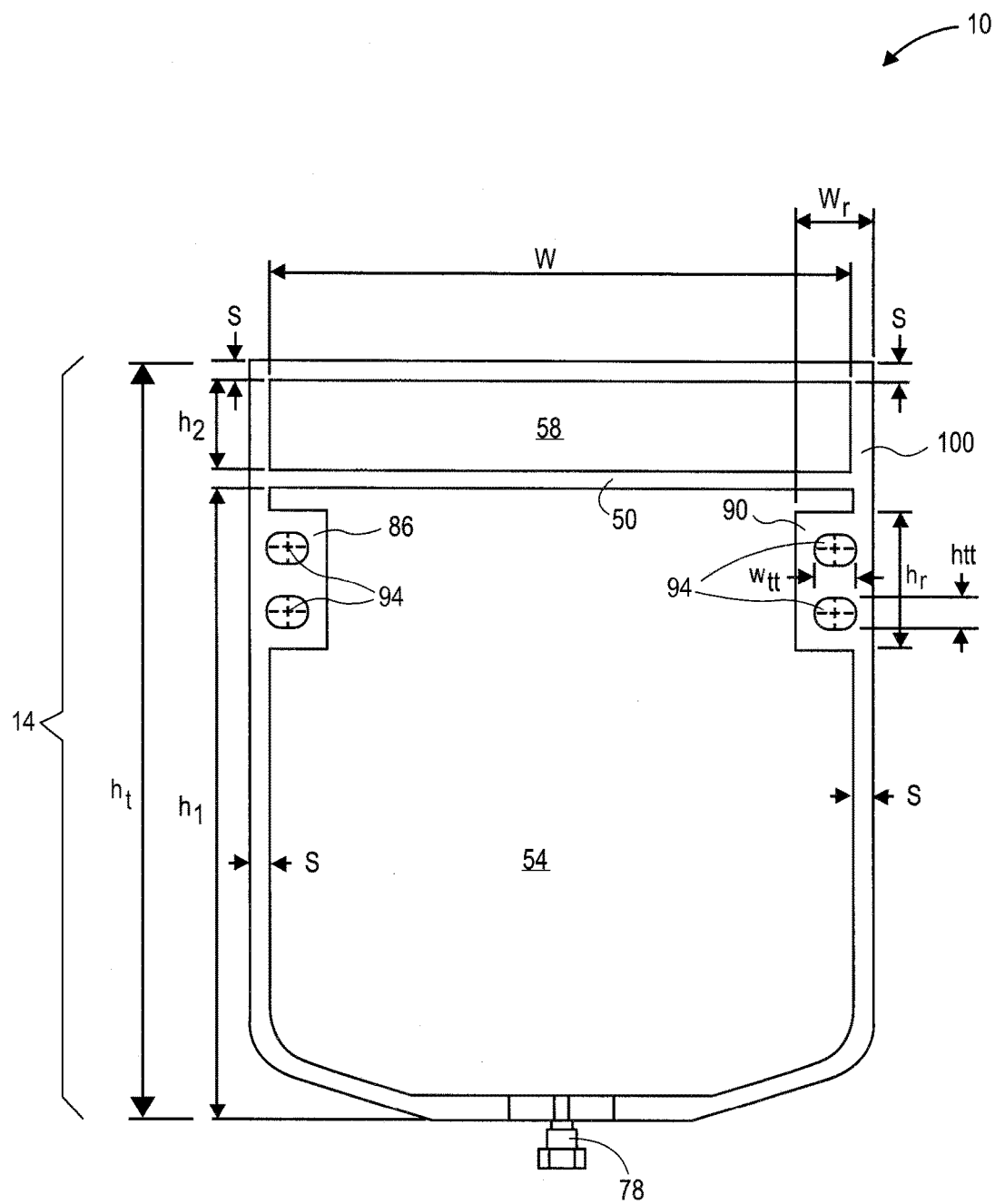
FIG. 5 is a top view of a package according to another embodiment and including a first compartment and a second compartment.
Figure 6:
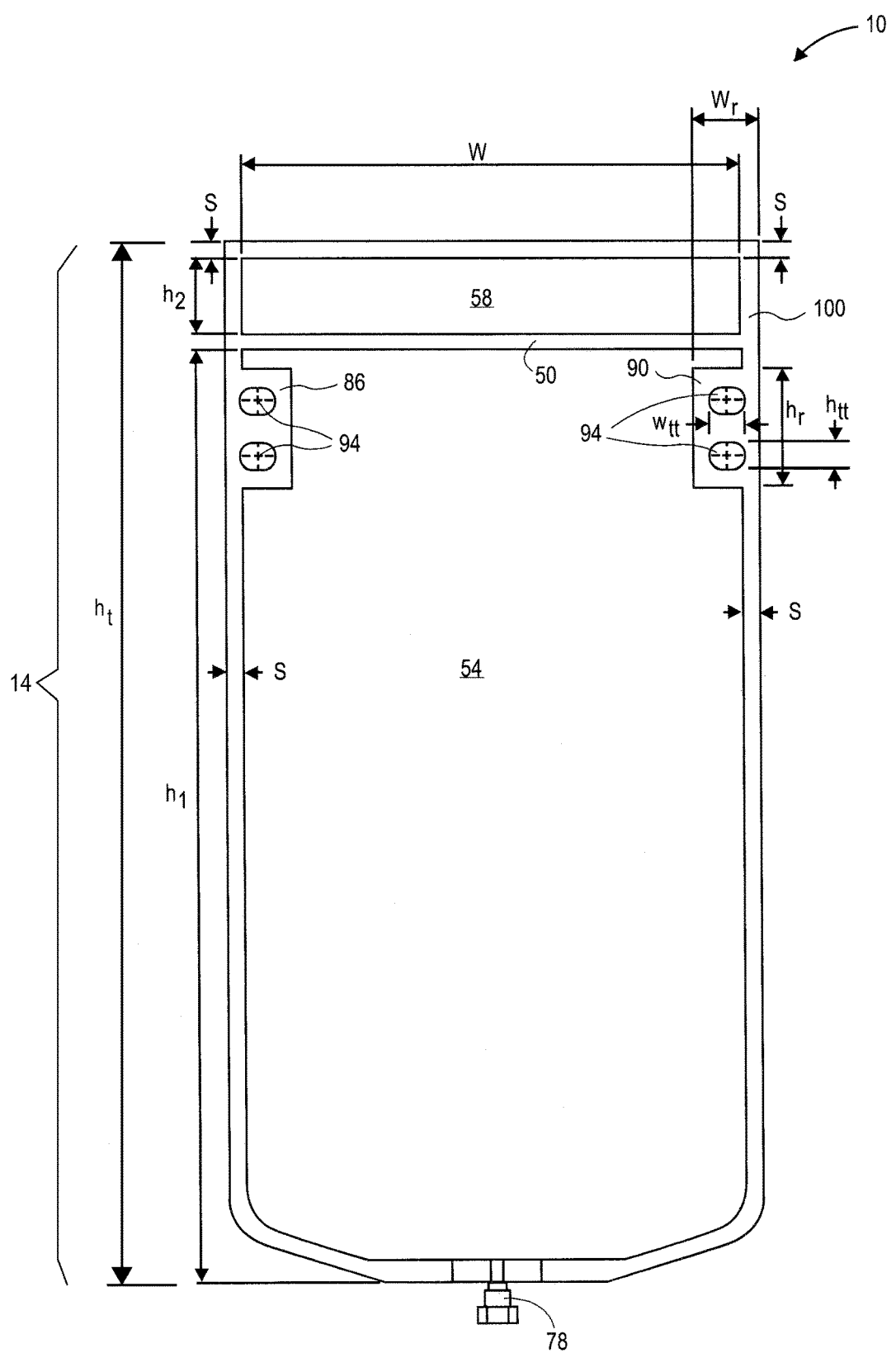
FIG. 6 is a top view of a package according to another embodiment and including a first compartment and a second compartment.

Each of the first compartment 54 and the second compartment 58, and therefore the package 10, may have any suitable dimensions. For example and as illustrated in FIGS. 5 and 6, which illustrate two potential packages 10 having different dimensions, the first and second compartments 54, 58 may have a width W in the range of approximately 6 inches to approximately 80 inches. The first and second compartments 54, 58 may have a width W of about 6, about 8, about 10, about 15, about 20, about 25, about 30, about 35, about 40, about 45, about 50, about 55, about 60, about 65, about 70, about 75, or about 80 inches, including any range therein (e.g., about 6 inches to about 55 inches, about 20 inches to about 25 inches, etc.).

The first compartment 54 may have a narrower width W near the valve 78, as illustrated in FIGS. 1-6. Further, the first compartment 54 may have a height $h_1$ of approximately 6 inches to approximately 80 inches, while the second compartment 58 may have a height $h_2$ of approximately 1 inch to approximately 30 inches. The first compartment 54 may have a height $h_1$ of about 6, about 8, about 10, about 15, about 20, about 25, about 30, about 35, about 40, about 45, about 50, about 55, about 60, about 65, about 70, about 75, or about 80 inches, including any range therein (e.g., about 6 inches to about 55 inches, about 20 inches to about 25 inches, etc.).

The second compartment 58 may have a height $h_2$ of about 1, about 3, about 6, about 9, about 12, about 15, about 18, about 21, about 24, about 27, or about 30 inches, including any range therein (e.g., about 1 inch to about 24 inches, about 9 inches to about 12 inches, etc.).

The package may, therefore, have an overall height $h_t$ of approximately 7 inches to approximately 130 inches, including about 7, about 14, about 21, about 28, about 35, about 42, about 49, about 56, about 63, about 70, about 77, about 84, about 91, about 98, about 105, about 112, about 119, about 126, about 127, about 128, about 129, or about 130 inches, including any range therein (e.g., about 7 inches to about 119 inches, about 42 to about 49 inches, etc.).

The peripheral seal 100 of the package 10 and the breakable seal 50 between the two compartments 54, 58 may have a dimensions of about 0.15 inches to about 3.5 inches, or about 0.15, about 0.3, about 0.6, about 0.9, about 1.2, about 1.5, about 1.8, about 2.1, about 2.4, about 2.7, about 3, about 3.1, about 3.2, about 3.3, about 3.4, or about 3.5 inches, including any range therein (e.g., about 0.15 inches to about 3.3 inches, about 2.7 inches to about 3 inches, etc.). The reinforced areas 86, 90 may be wider than the peripheral seal 100 by about 0.5 inches to about 20 inches, or about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, or about 20 inches, including any range therein (e.g., about 0.5 inches to about 8 inches, about 3.5 inches to about 4 inches, etc.). Therefore, the width of $W_r$ is in the range of about 0.615 inches to about 23.5 inches, or about 0.615, about 0.715, about 0.815, about 0.915, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, about 20, about 20.5, about 21, about 21.5, about 22, about 22.5, about 23, or about 23.5 inches, including any range therein (e.g., about 0.615 inches to about 8.5 inches, about 7 inches to about 7.5 inches, etc.).

In embodiments incorporating reinforced areas, the height $h_r$ of the reinforced areas 86, 90 may be in the range of about 0.5 inches to about 20 inches, or about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, or about 20 inches, including any range therein (e.g., about 0.5 inches to about 14 inches, about 6 inches to about 6.5 inches, etc.).

In embodiments that include reinforced areas, the dimensions of the reinforced areas 86, 90 may depend on how many and the size of the through-holes 94. In the illustrative embodiment, the through-holes 94 have ovular apertures measuring about 0.25 inches to about 7.5 inches wide ($w_{tt}$), or about 0.25, about 0.5, about 0.75, about 1, about 1.5, about 2, about 2.5, about 3, about 3.5, about 4, about 4.5, about 5, about 5.5, about 6, about 6.5, about 7, or about 7.5 inches wide ($w_{tt}$), including any range therein (e.g., about 0.25 inches to about 1.5 inches, about 2.5 inches to about 3 inches, etc.), and about 0.25 inches to about 7.5 inches high ($h_{tt}$), or about 0.25, about 0.5, about 0.75, about 1, about 1.5, about 2, about 2.5, about 3, about 3.5, about 4, about 4.5, about 5, about 5.5, about 6, about 6.5, about 7, or about 7.5 inches high ($h_{tt}$), including any range therein (e.g., about 0.25 inches to about 1.5 inches, about 2.5 inches to about 3 inches, etc.).

The package 10 includes a first state and a second state. The first state comprises the package 10 with the breakable seal 50 separates the first compartment 54 and the second compartment 58. The second state comprises the breakable seal 50 being at least partially broken so as to allow for the combining of the first substance 62 and the second substance 66. With respect to FIGS. 1 and 3, in the first state, the breakable seal 50 is intact, thereby isolating the first compartment 54 from the second compartment 58 such that the first substance 62 is separate from the second substance 66. With respect to FIGS. 2 and 4, the breakable seal 50 is broken such that the first compartment 54 and the second compartment 58 are in fluid communication. As such, the first substance 62 and the second substance 66 mix to form, e.g., the solution 70. In a preferred embodiment, the second substance 66 is soluble in the first substance 62. In certain embodiments, the solution 70 has a pH of from pH 8 to pH 12.

In operation, the package 10 may be transported to a site of use in the first state. When it is desired that the first substance 62 be mixed with the second substance 66, the user applies force or pressure in order to facilitate breaking the breakable seal 50. For example, the user may apply force or pressure to the exterior surface 34 of each of the walls 18, 22 at a location near the breakable seal 50. The force transitions the package 10 from the first state to the second state. As such, the breakable seal 50 is broken and the two compartments 54, 58 are no longer isolated from one another. The pressure exerted on the package 10 may be at a pounds per square inch (psi) of about 5, about 10, about 15, about 20, about 25, about 30, about 45, about 50, about 55, or about 60 psi, including any range therein (e.g., about 5 psi to about 60 psi, about 20 psi to about 25 psi, etc.). The user may then shake or agitate the package 10 to facilitate mixing the combined substance. The solution may be selectively expelled through the nozzle 78.

The first substance 62 may be a solvent that dissolves a solute resulting in a solution. The solvent may comprise, but is not limited to, water, an acidic solution, a basic solution, an oil, an alcohol, a detergent, a surfactant, and combinations thereof. The solvent may be non-polar, polar aprotic, or polar protic. Exemplary embodiments of non-polar solvents include, but are not limited to, pentane, cyclopentane, hexane, cyclohexane, benzene, toluene, 1,4-dioxane, chloroform, and diethyl ether. Exemplary embodiments of polar aprotic solvents include, but are not limited to, dichloromethane, tetrahydrofuran, ethyl acetate, acetone, dimethylformamide, acetonitrile, dimethyl sulfoxide, and propylene carbonate. Exemplary embodiments of polar proteic solvents include, but are not limited to, formic acid, n-butanol, isopropanol, n-propanol, ethanol, methanol, acetic acid, nitromethane, and water. The first substance may have a pH of from about 3 to about 12, including a pH of about 3, about 4, about 5, about 6, about 7, about 8, about 9, about 10, about 11, or about 12, including any range therein (e.g., about 3 to about 8, about 4 to about 5, etc.). In certain embodiments, the first substance has a pH of from pH 8 to pH 12.

In certain embodiments of the package, the second substance 66 is a substance is soluble when combined with the first substance 62. In certain embodiments, the second substance is a solid. The second substance may comprise a reagent for water analysis, a chelant, an inert fluorescing agent, and/or a salt. The package 10 may further include an N-th substance in an N-th compartment, wherein the N-th substance has a pH of about 3 to about 12.

In certain embodiments of the package, the first substance and/or the second substance comprises a reagent for water analysis, which may include a reactive dye. In certain embodiments, the reagent for water analysis is a magnesium coordinating fluorescing reagent, i.e., a chemical compound that is capable of reacting with soluble magnesium to produce a coordinated magnesium compound with fluorescing properties. Certain magnesium coordinating fluorescing reagents comprise at least one water soluble, aromatic ortho hydroxyl substituted azo dye. Exemplary embodiments of magnesium coordinating fluorescing reagents include, but are not limited to, Plasmocorinth B, Eriochrome Black T, Calmagite, 8-hydroxyquinolone-5-sulfonic acid ("HQS"), and combinations thereof. In certain embodiments, the second substance is HQS.

In certain embodiments of the package, the first substance and/or the second substance comprises a chelant. Exemplary embodiments of chelants include, but are not limited to, EDTA salts, CDTA salts, ethylenediamine, crown ethers, cryptands, and combinations thereof. In certain embodiments wherein the first substance and/or second substance comprises a chelant, the chelant is magnesium CDTA ("MgCDTA"). In certain embodiments, the first substance comprises a chelant.

In certain embodiments of the package, the first substance and/or the second substance further comprises an inert fluorescing agent (e.g., an inert dye). When utilized, the inert fluorescing agent should be selected such that (a) the agent does not react with other species (i.e., is inert), and (b) the agent's fluorescence wavelength should not interfere with the wavelengths of the other fluorescing species. In certain embodiments, the inert fluorescing agent is selected from the group consisting of a derivative of rhodamine, a derivative of fluorescein, and combinations thereof. In certain embodiments, the first substance comprises an inert fluorescing agent, and the inert fluorescing agent may be Rhodamine WT.

In certain embodiments of the package, the first substance and/or the second substance further comprises a salt, which in certain embodiments is an inorganic salt, which may include one or more alkali and/or alkaline earth halides. Exemplary embodiments of salts include, but are not limited to, sodium chloride, potassium chloride, and combinations thereof. In certain embodiments, the first substance comprises a salt.

The package may further include an n-th substance in an n-th compartment, wherein the n-th substance comprises any of the aforementioned ingredients, and combinations thereof, and may have a pH of from about 3 to about 12.

The body 14 of the package 10 may comprise a polymer blend further comprising one or more additional components, such as one or more additives. Suitable additives include, but are not limited to, an impact modifier, a colorant, a flame retardant, a heat stabilizer, a plasticizer, a lubricant, a mold release agent, a filler (organic and/or inorganic), a reinforcing agent, an antioxidant agent, an antistatic agent, a blowing agent, an anti-drip agent, and a radiation stabilizer (e.g., a UV stabilizer and/or a gamma stabilizer). In addition, surface additives can be added to the body 14. The selection and amount of the one or more additives depend on various factors that would be recognized by one of ordinary skill the art, including, but not limited to, end-use requirements and/or effect on flame retardancy, and/or impact strength.

Methods of Manufacture

The polymer or polymer blend compositions may be formed, shaped, molded or injection molded into the body 14 of the package 10. The compositions can be molded into useful shaped packages by a variety of means such as injection molding, extrusion, rotational molding, blow molding and thermoforming to form the package. In certain embodiments, the body 14 of the package 10 may have a biocontent according to ASTM-D6866 of about 0.01 weight %, about 0.1 weight %, about 0.5 weight %, about 1 weight %, about 2 weight % to about 90 weight %, or at least about 2 weight %, about 3 weight %, about 4 weight %, about 5 weight %, about 6 weight %, about 7 weight %, about 8 weight %, about 9 weight %, about 10 weight %, about 11 weight %, about 12 weight %, about 13 weight %, about 14 weight %, about 15 weight %, about 16 weight %, about 17 weight %, about 18 weight %, about 19 weight %, about 20 weight %, about 25 weight %, about 30 weight %, about 35 weight %, about 40 weight %, about 45 weight %, about 50 weight %, about 55 weight %, about 60 weight % or about 65 weight %, to about 90 weight %.

In certain embodiments of the package 10, the breakable seal 50 is manufactured by a flat bar weld with constant pressure at a melt temperature of the thermoplastic polymer. By controlling the heat energy, the force in which the interior surfaces 38 of the first and second walls 18, 22 are pressed together, and the duration of the heat energy applied, the breakable seal 50 is created. The breakable seal 50 is designed and constructed so as to be temporary, and preferably is configured to be strong enough to remain intact until acted upon by force or pressure (i.e., a physical force) when the substances 62, 66 of the first and second compartments 54, 58, respectively, are to be combined. In embodiments where the breakable seal 50 is created by flat bar weld, the strength of the breakable seal 50 may be altered by, for example, reducing the time the first and second walls 18, 22 are exposed to heat, or reducing the heat used to create the breakable seal 50. The breakable seal 50 is able to remain sealed under some force or pressure that is less than a threshold amount of force or pressure, but will begin to break once the threshold force or pressure is reached. The amount of force or pressure required to break the breakable seal 50 is less than that of a traditional seal (e.g., peripheral seal 100). Therefore, the breakable seal 50 breaks under force or pressure prior to the side walls 18, 22 becoming damaged. The breakable seal 50 may be hermetic or non-hermetic, depending upon the requirements of the package 10.

Methods of Use

The package may be applied in any industry, including medical, healthcare, waste water, pulp/paper, coal, oil/gas, food/beverage, environmental, industrial water, energy services, power/utilities, waste management, retail (including food retail), food service, food safety, housekeeping, laundry, lodging, pest elimination, pool/spa, restaurant, restroom, ware washing, automotive, electronics, air protection, catalyst, chemicals, monitoring/control, automation, mining, soaps/detergent, pharmaceuticals, cosmetic, agriculture, dairy, and/or farming.

The package may be used in particular with industrial water analysis applications, for example, to measure concentration of certain chemical substances that may cause, for example, corrosion and/or scaling. Therefore, in a preferred embodiment, the first substance 62 comprises water while the second substance 66 comprises a reactant. The first substance 62 and/or the second substance 66 may further comprise a corrosion inhibitor and/or a scale inhibitor. Once the breakable seal 50 is broken, water of the first substance 62, when present, dissolves the reactant of second substance 66, when present, thereby allowing for use of the solution 70 in analytical testing. In a particularly preferred embodiment, the package and ingredients contained therein are particularly useful to fluorometrically analyze for magnesium concentration in water, more particularly in boiler feed water.

Any patents referred to herein, are hereby incorporated herein by reference, whether or not specifically done so within the text of this disclosure.

To the extent that the terms "include," "includes," or "including" are used in the specification or the claims, they are intended to be inclusive in a manner similar to the term "comprising" as that term is interpreted when employed as a transitional word in a claim. Furthermore, to the extent that the term "or" is employed (e.g., A or B), it is intended to mean "A or B or both A and B." When the applicants intend to indicate "only A or B but not both," then the term "only A or B but not both" will be employed. Thus, use of the term "or" herein is the inclusive, and not the exclusive use. See Bryan A. Garner, A Dictionary of Modern Legal Usage 624 (2d ed. 1995). Also, to the extent that the terms "in" or "into" are used in the specification or the claims, it is intended to additionally mean "on" or "onto." Furthermore, to the extent that the term "connect" is used in the specification or the claims, it is intended to mean not only "directly connected to," but also "indirectly connected to" such as connected through another component or components. In the present disclosure, the words "a" or "an" are to be taken to include both the singular and the plural. Conversely, any reference to plural items shall, where appropriate, include the singular.

All ranges and parameters disclosed herein are understood to encompass any and all sub-ranges assumed and subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more (e.g., 1 to 6.1), and ending with a maximum value of 10 or less (e.g., 2.3 to 9.4, 3 to 8, 4 to 7), and finally to each number 1, 2, 3, 4, 5, 6, 7, 8, 9, and 10 contained within the range.

The general inventive concepts have been illustrated, at least in part, by describing various exemplary embodiments thereof. While these exemplary embodiments have been described in considerable detail, it is not the Applicant's intent to restrict or in any way limit the scope of the appended claims to such detail. Furthermore, the various inventive concepts may be utilized in combination with one another (e.g., first, second, third, fourth, etc., exemplary embodiments may be utilized in combination with each other). Additionally, any particular element recited as relating to a particularly disclosed embodiment should be interpreted as available for use with all disclosed embodiments, unless incorporation of the particular element would be contradictory to the express terms of the embodiment. Additional advantages and modifications will be readily apparent to those skilled in the art. Therefore, the disclosure, in its broader aspects, is not limited to the specific details presented therein, the representative apparatus, or the illustrative examples shown and described. Accordingly, departures may be made from such details without departing from the spirit or scope of the general inventive concepts.

What is claimed is:

1. A method of analyzing one or more properties of an aliquot of water comprising:
    breaking a breakable seal of a package via physical force, the package comprising a body having a first compartment comprising a first substance, a second compartment comprising a second substance, and the breakable seal that separates the first and second compartments, thereby forming a mixture comprising the first and second substances;
    adding the mixture to an aliquot of water; and
    analyzing the one or more properties of the aliquot of water;
    wherein the first substance is a liquid solvent comprising water and the second substance is a point-of-use reagent soluble when combined with the first substance and comprises a magnesium coordinating fluorescing reagent.

2. The method of claim 1, wherein the aliquot of water further comprises magnesium.

3. The method of claim 1, wherein the aliquot of water is an aliquot of boiler system feed water.

4. The method of claim 1, wherein breaking the breakable seal comprises an application of physical force on an exterior surface of the body.

5. The method of claim 1, wherein the first substance has a pH of from pH 8 to pH 12.

6. The method of claim 1, wherein the first substance has a pH of about pH 3 to about pH 12.

7. The method of claim 1, wherein the second substance further comprises at least one of a chelant, an inert fluorescing agent, and a salt.

8. The method of claim 1, wherein the magnesium coordinating fluorescing reagent is selected from Plasmocorinth B, Eriochrome Black T, Calmagite, 8-hydroxyquinolone-5-sulfonic acid ("HQS"), and combinations thereof.

9. The method of claim 1, wherein the magnesium coordinating fluorescing reagent is 8-hydroxyquinolone-5-sulfonic acid ("HQS").

10. The method of claim 1, wherein the magnesium coordinating fluorescing reagent is a solid.

11. The method of claim 1, wherein the magnesium coordinating fluorescing reagent is Plasmocorinth B.

12. The method of claim 1, wherein the magnesium coordinating fluorescing reagent is Eriochrome Black T.

13. The method of claim 1, wherein the magnesium coordinating fluorescing reagent is Calmagite.

14. The method of claim 1, wherein the first substance further comprises an inert fluorescing agent.

15. The method of claim 14, wherein the first substance further comprises a water soluble, non-coordinating base.

16. The method of claim 1, wherein the body of the package is constructed of a thermoplastic polymer.

17. The method of claim 16, wherein the thermoplastic polymer is selected from polyethylene, polypropylene, polystyrene, polyethylene terephthalate, nylon, polycarbonate, polyvinyl chloride, polytetrafluoroethylene, polyurethane, polyamide, polyacrylamide, copolymers thereof, and blends thereof.

18. The method of claim 1, wherein the first substance further comprises a chelant.

19. The method of claim 18, wherein the chelant is selected from EDTA salts, CDTA salts, ethylenediamine, crown ethers, cryptands, and combinations thereof.

20. The method of claim 18, wherein the chelant is magnesium CDTA.

* * * * *

UNITED STATES PATENT AND TRADEMARK OFFICE
CERTIFICATE OF CORRECTION

PATENT NO. : 10,078,073 B2
APPLICATION NO. : 14/483634
DATED : September 18, 2018
INVENTOR(S) : Arthur J. Kahaian et al.

It is certified that error appears in the above-identified patent and that said Letters Patent is hereby corrected as shown below:

On the Title Page

Item (72), please delete "Sasha J. Welz" and insert --Sascha J. Welz--

Signed and Sealed this
Fifth Day of March, 2019

Andrei Iancu
*Director of the United States Patent and Trademark Office*